United States Patent
Ray

(10) Patent No.: US 6,443,956 B1
(45) Date of Patent: Sep. 3, 2002

(54) VERTEBRAL DRILL BIT AND INSERTER

(75) Inventor: Terry L. Ray, Gilbert, AZ (US)

(73) Assignee: Mekanika, Inc., Deerfield Beach, FL (US)

( * ) Notice: Subject to any disclaimer, the term of this patent is extended or adjusted under 35 U.S.C. 154(b) by 123 days.

(21) Appl. No.: 09/668,400

(22) Filed: Sep. 22, 2000

(51) Int. Cl.⁷ .............................................. A61B 17/00
(52) U.S. Cl. ........................................................ 606/80
(58) Field of Search ..................... 606/80, 79; 408/214, 408/225; 433/102, 165

(56) References Cited

U.S. PATENT DOCUMENTS

| | | | | |
|---|---|---|---|---|
| 5,380,333 A | * | 1/1995 | Meloul et al. ................. | 606/80 |
| 5,562,371 A | * | 10/1996 | Reed ........................... | 408/225 |
| 5,573,537 A | * | 11/1996 | Rogozinski ................... | 606/80 |
| 5,931,841 A | * | 8/1999 | Ralph ........................... | 606/80 |
| 5,968,048 A | * | 10/1999 | Harder ......................... | 606/80 |
| 6,238,398 B1 | * | 5/2001 | Lechot ......................... | 606/80 |

* cited by examiner

*Primary Examiner*—Todd E. Manahan
(74) *Attorney, Agent, or Firm*—Parsons & Goltry; Robert A. Parsons; Michael W. Goltry

(57) ABSTRACT

A vertebral drill bit for forming a pathway through a pedicle into a vertebral body. The vertebral drill bit includes a cutting shank having a generally uniform diameter, an attachment head at one end of the cutting shank and a tip at the other end of the cutting shank. Also included is a point at which the diameter of the cutting shank at the second end begins to get smaller to form the tip. A flute is formed in the cutting shank and extends from the end to the tip. An edge of the flute from the first end to proximate the point is sharp for cutting, while edges of the flute from the point to the tip are rounded.

17 Claims, 3 Drawing Sheets

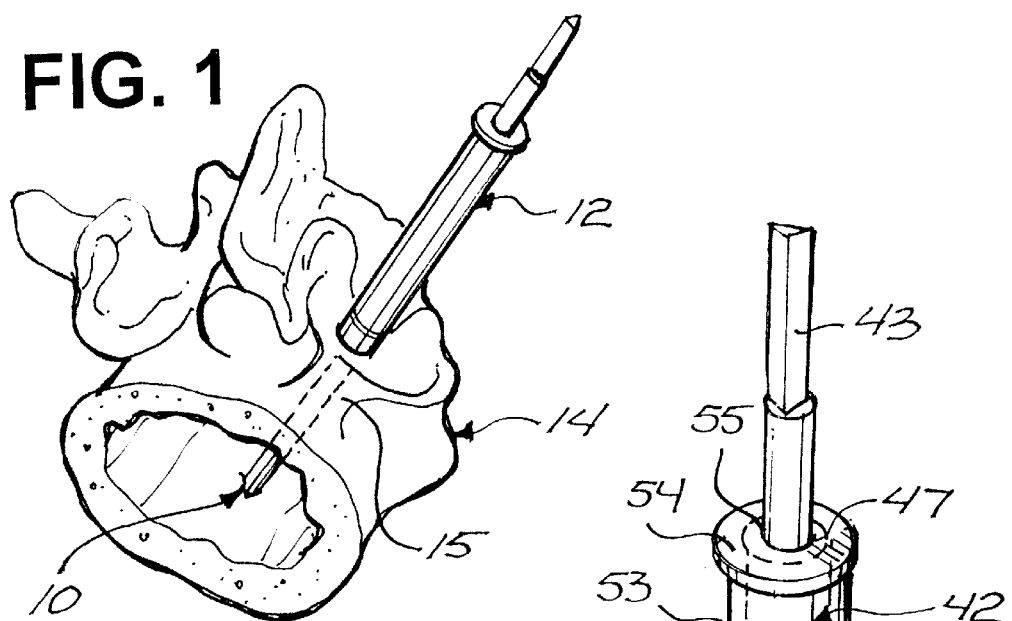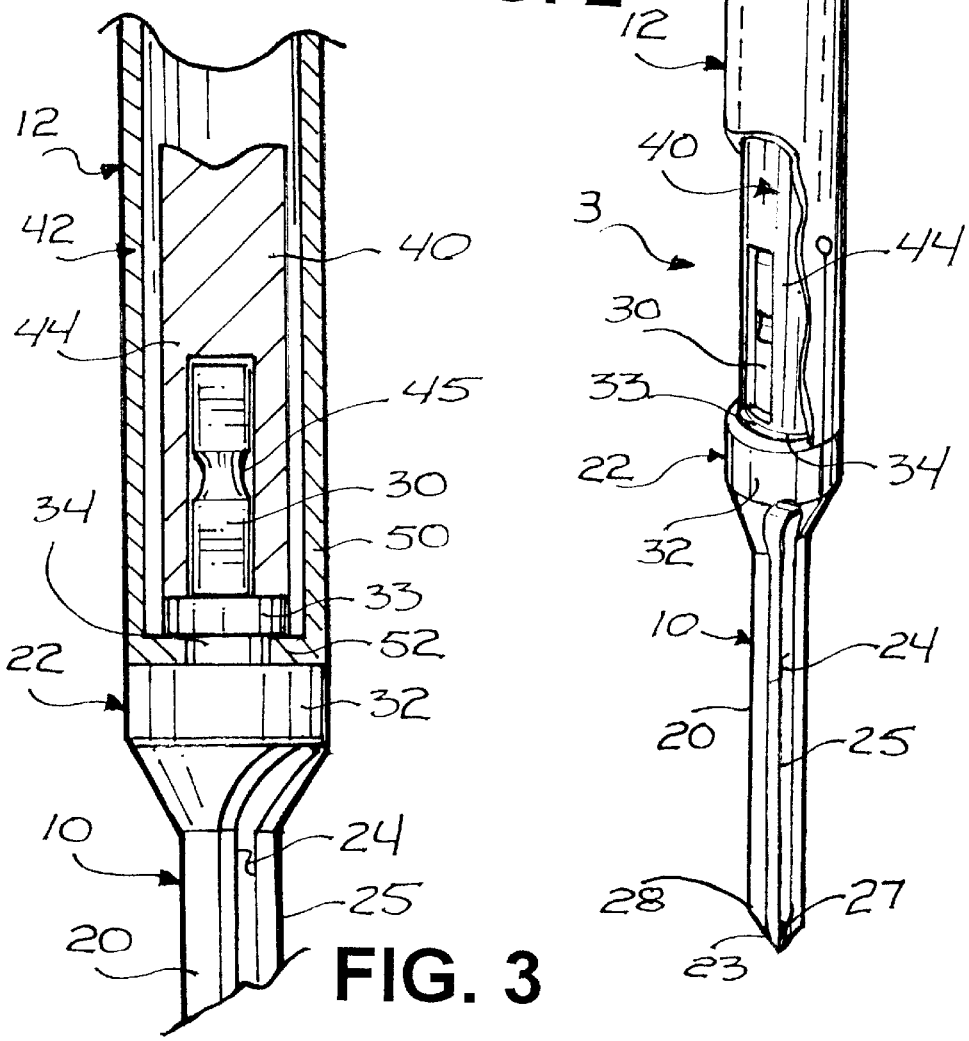

VERTEBRAL DRILL BIT AND INSERTER

FIELD OF THE INVENTION

This invention relates to medical instruments.

More particularly, the present invention relates to devices for spinal fixation

In a further and more specific aspect, the instant invention concerns positioning and placement of pedicle screws.

BACKGROUND OF THE INVENTION

Injuries to the spinal column have always been numerous and debilitating. Only recently have techniques been developed to reduce effects of injuries and wear on the vertebrae. Spinal fixation employing screws inserted into the pedicles of the vertebrae is a well accepted technique. The force nucleus of the normal vertebrae is located at the base of the superior process at a point where the ridge on the pars interarticularis, the ridge on the superior facet, and the ridge on the transverse process all converge. Opening the cortical bone at this point permits access to the intermedullary canal of the pedicle through which the screw passes into the vertebral body. Generally, screws are inserted into a number of vertebrae and fix plates in position for stabilization of a portion of the spinal column.

Each screw is inserted by first locating the proper area either visually or by the use of a probe. When the proper location (force nucleus) is located, an opening is typically formed in the cortical bone using a rongeur or gouge. Once a portion of the cortical bone has been removed, a pedicle probe is employed to probe the pedicle. The probe is inserted with its tip perpendicular to the horizontal plane. A gentle back-and-forth or wiggle motion is used to advance the probe through the cancellous bone within the pedicle. It is desirous that the angled tip of the probe follow the cancellous tube of bone to the vertebral body. However, often the probe will sharply exit the pedicle. If this occurs, a ball tip probe must be employed outside the pedicle to determine if the probe has indeed exited the pedicle. This can be a serious problem if the probe exits into the vertebral foramen. Often the physician will manipulate the probe in such a manner as to insure that an exit does not occur into the vertebral foramen. This, however, often has the result of over compensation and an exit in a different location.

After the probe reaches the vertebral body, the probe is withdrawn and a marker is inserted. Intraoperative x-rays are taken to confirm positioning, before the screws are inserted. After the exploratory probe has been completed, each pathway must be widened with a tap of appropriate dimensions. The pedicle screw is then positioned.

While effective, current placement of pedicle screws is time consuming due to the number of steps, including penetrating the cortex, probing the pedicle, confirming the positioning, tapping the pathway, and inserting the screw. Furthermore, the skill needed to perform this procedure, particularly the step of probing, is very great. While following the path of least resistance, namely the cancellous tube through the pedicle, sounds straight forward, it is very difficult. The cancellous tube is bone, and although less resistant than the cortex, still requires pressure to force the probe through. A great deal of "feel" and control is needed to avoid exiting the pedicle. Even with highly skilled individuals, many exits occur. While generally not injurious, this slows the process even more. There is also the chance of injury to the spinal cord and/or nerve roots if the exit occurs into the vertebral foramen. The high level of skill required and the time required translates into increased expense.

It would be highly advantageous, therefore, to remedy the foregoing and other deficiencies inherent in the prior art.

Accordingly, it is an object of the present invention to provide a new vertebral drill bit and inserter.

Another object of the invention is to provide a vertebral drill bit which is self guiding.

And another object of the invention is to provide a vertebral drill bit which will reduce exits from the pedicle.

Still another object of the present invention is to provide a vertebral drill bit which can be employed to confirm positioning.

Yet another object of the invention is to provide a vertebral drill which is relatively quick and easy to use.

SUMMARY OF THE INVENTION

Briefly, to achieve the desired objects of the instant invention in accordance with a preferred embodiment thereof, provided is a vertebral drill bit for forming a pathway through a pedicle into a vertebral body. The drill bit includes a cutting shank having a first end and a second end and a generally uniform diameter therebetween, an attachment head at the first end of the cutting shank and a tip at the second end of the cutting shank. Also provided is a point at which the diameter of the cutting shank at the second end begins to get smaller to form the tip. A flute is formed in the cutting shank and extends from the first end to the tip. An edge of the flute from the first end to proximate the point is sharp for cutting, and edges of the flute from the point to the tip are rounded.

Also provided in another embodiment is an inserter for coupling the drill bit to a drill. The inserter includes a chuck end and a receiver end.

BRIEF DESCRIPTION OF THE DRAWINGS

The foregoing and further and more specific objects and advantages of the instant invention will become readily apparent to those skilled in the art from the following detailed description of a preferred embodiment thereof taken in conjunction with the drawings, in which:

FIG. 1 is a perspective view of the drill bit and inserter of the present invention, as it appears forming a pathway in a pedicle;

FIG. 2 is an isometric view of the drill bit and inserter of FIG. 1 with portions thereof removed;

FIG. 3 is a partial sectional side view of the drill bit and inserter of FIGS. 1 and 2;

DETAILED DESCRIPTION OF THE PREFERRED EMBODIMENT

Figures 4, 5:
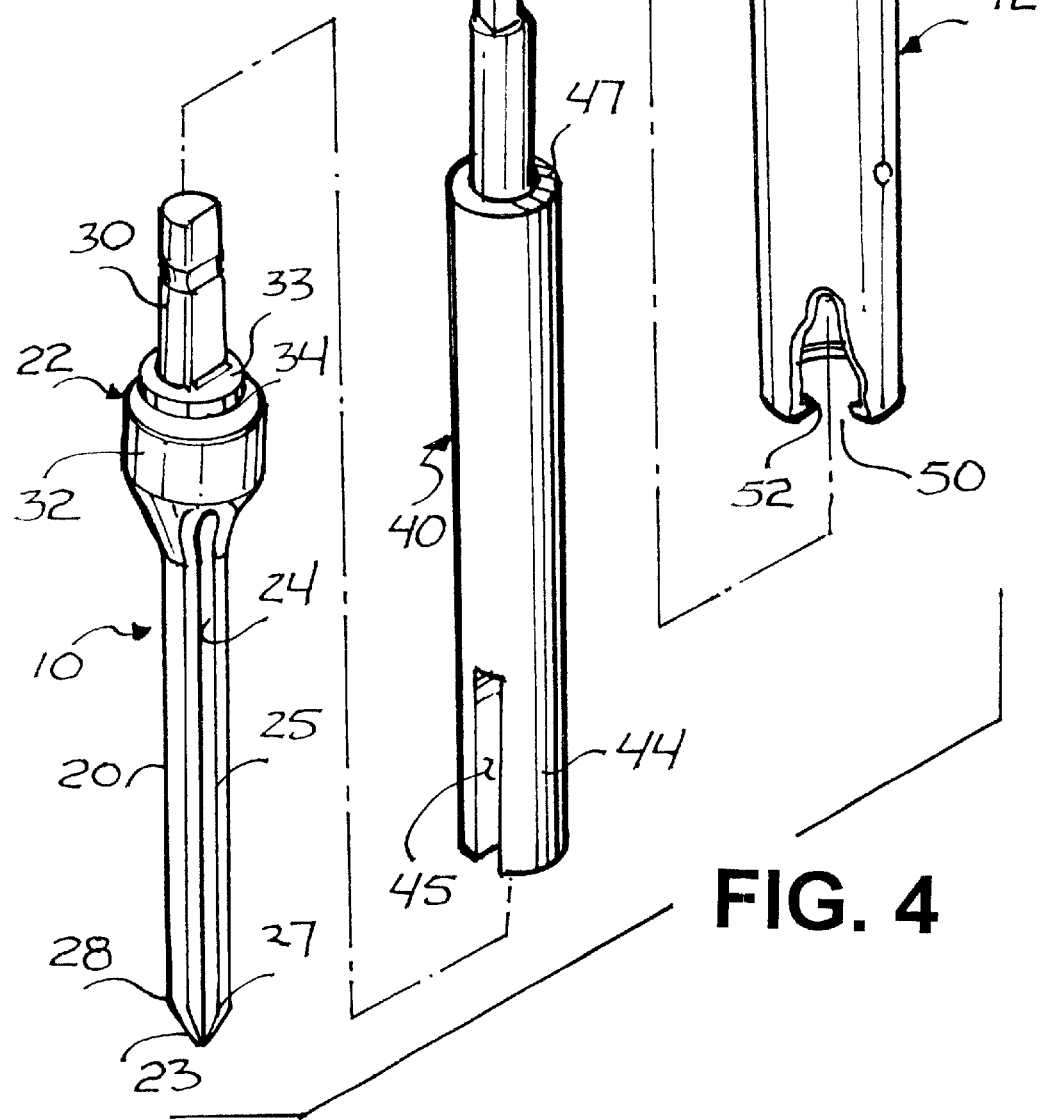
FIG. 4 is an exploded isometric view of the drill bit and inserter of FIGS. 1–3.
FIG. 5 is a view of another embodiment of an attachment shank of a drill bit.

Turning now to the drawings in which like reference characters indicate corresponding elements throughout the several views, attention is first directed to FIG. 1 which illustrates a drill bit 10 carried by an inserter 12 inserted into a vertebrae 14. Drill bit 10 has formed a pathway through a pedicle 15 of vertebrae 14. The pathway is well known to those skilled in the art and includes an opening formed in the force nucleus of vertebrae 14. The force nucleus is located at the base of the superior process at a point where the ridge on the pars interarticularis, the ridge on the superior facet, and the ridge. on the transverse process all converge. Opening the cortical bone at this point permits access to the intermedullary canal of the pedicle formed of cancellous bone. When the proper location (force nucleus) is located, an opening is formed in the cortical bone using any conventional technique such as using a rongeur or gouge. Once a portion of the cortical bone has been removed, the pathway is completed by drilling through the cancellous bone to the vertebral body using drill bit 10. Once the pathway has been formed, the drill bit can be employed as a marker during an x-ray procedure to confirm positioning. In this illustration inserter 12 is employed to coupled drill bit 10 to a drill (not shown). As will become evident, various other inserters can be employed to couple a drill bit to the drill, some of which will be described as different embodiments. Additionally, different embodiments of attachment structures for attaching the drill bit to the inserter will be described. Each will be employed in substantially the same manner as described herein.

Turning now to FIGS. 2–4, drill bit 10 and inserter 12 are illustrated. Drill bit 10 includes a cutting shank 20 having an attachment head 22 at one end and a tip 23 at an opposing end. Cutting shank 20 flares proximate attachment head 22, to substantially match the diameter thereof. At least one flute 24 extends the length of cutting shank 20 from tip 23 to attachment head 22. Flute 24 has a sharp edge 25 extending its entire length except at tip 23. Both edges of flute 24 can be sharp if desired. Rounded or dull edges 27 are formed at tip 23 for purposes which will be described presently. The transition between sharp edge 25 and dull edges 27 is preferably located at a point 28 where tip 23 ends and cutting shank 20 reaches a substantially uniform or tapering width clearly definable from the greater slope of tip 23. It will be understood that sharp edge 25 can start further back toward attachment head 22, but not further forward toward tip 23. Flute 24 extends into the flared portion with cutting edge 25 also flaring.

When forming the pathway through pedicle 15, cutting edge or edges 25 cut through the cancellous bone following the intermedullary canal into the vertebral body. Dull edges 27 at tip 23 are incapable of cutting through cortical bone, and thus will be deflected by the walls of pedicle 15. Drill bit 10 will therefore remain within the intermedullary canal and not exit through the wall of pedicle 15. In this manner, a self guiding drill bit is provided. As mentioned previously, drill bit 10 is started in the pedicle through an opening formed through the cortical bone using conventional methods. The flared portion of cutting shank 20 and the corresponding flared portion of sharp edge 25 form a counter sink in the cortical bone. This is formed to receive the intergal nut of conventional screws used in this procedure. It also starts the threads of the screws. While a single flute 24 is illustrated, it will be understood by those skilled in the art that additional flutes can be formed in cutting shank 20, as long as the edges are rounded or dull at tip 23 to prevent cutting through cortical bone.

Still referring to FIGS. 2–4, drill bit 10 is attached to inserter 12 by attachment head 22. Attachment head 22 includes an attachment shank 30 extending from a portion 32 terminating the flared end of cutting shank 20. Attachment shank 30 has a smaller diameter than portion 32, and is divided by an enlargement 33 forming a groove 34 adjacent portion 32. Enlargement 33 also has a smaller diameter than portion 32.

Inserter 12 includes a receiver 40 and a securing sleeve 42. Receiver 40 has a shank end 43 for receipt within the chuck of a drill, and a receiver end 44 with a slot 45 formed therein. A shoulder 47 is formed between the greater diameter receiver end 44 and the lesser diameter shank end 43. Attachment shank 30 is fitted to be received by slot 45. In the preferred embodiment, attachment shank 30 includes flattened sides which lie flush with the sides of slot 45. Thus, relative rotation between drill bit 10 and receiver 40 is prevented. Various structures and shapes can be employed for attachment shank 30 so as to prevent relative rotation with receiver 40. With momentary reference to FIG. 5, another embodiment of an attachment shank 30' is illustrated. In this embodiment, only a single side has been flattened to prevent relative rotation. It will be understood by those skilled in the art that notches, slots, tabs, indents and various other shapes can be employed.

Referring back to FIGS. 2–4, securing sleeve 42 is generally tubular and has an outer diameter generally the same as the diameter of portion 32 or slightly less, thereby eliminating any protrusions likely to snag during insertion of the device. The inner diameter of securing sleeve 42 is large enough to accommodate receiver end 44 of receiver 40. An open end 50 of sleeve 42 terminates in an inwardly directed flange 52 and an opposing end 53 is closed by a stop 54 having an aperture 55 formed therein. Open end 50 is received over receiver 40 and engages drill bit 10 with flange 52 received in groove 34. Shank end 43 passes through aperture 55. Receiver 40 is prevented from being removed from end 53 by the engagement of shoulder 47 against stop 54. Shoulder 57 has a larger diameter than aperture 55.

Thus, receiver 40 and sleeve 42 interact to form inserter 12, firmly attaching drill bit 10 to a drill but allowing a toggle or pivoting movement of drill bit 10 due to the multiple connections. The toggling action of drill bit 10 permits it to conform to the slight angle adjustments needed to remain within the intermedullary canal and not exit through the wall of pedicle 15 during drilling.

Figure 6:
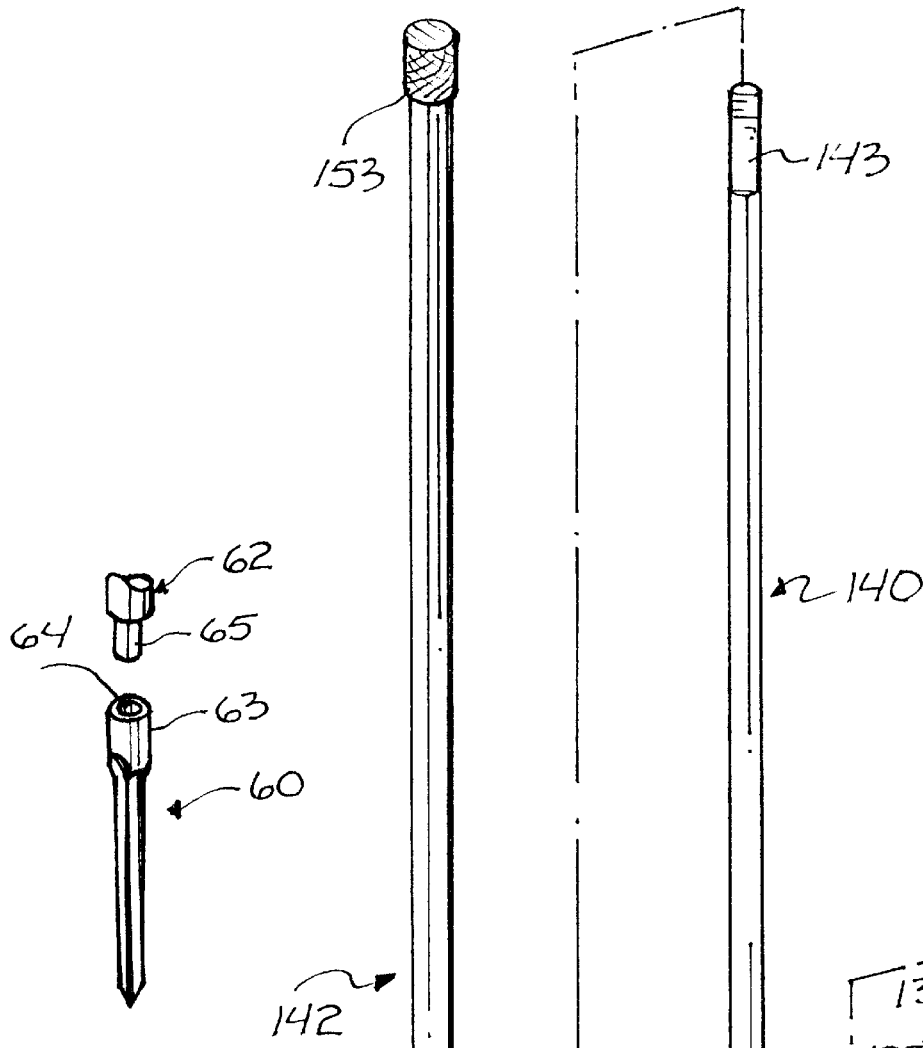
FIG. 6 is a partial perspective view of the engagement elements of another embodiment of a drill bit and inserter.

Turning now to FIG. 6, other embodiments of a drill bit 60 and an inserter 62 are illustrated. In this embodiment, drill bit 60 is generally identical to drill bit 10, with a different attachment head 63. Attachment head 63 includes a socket 64 formed therein. Socket 64 can have numerous shapes such as square, triangular, etc., but is preferably a hex shape. Inserter is a single length having a receiver end 65 shaped to be received within socket 64 and a chuck end, not shown, identical to chuck end 43. The loose connection between socket 64 and receiver end 65 permits toggling of drill bit 60.

Figure 7:
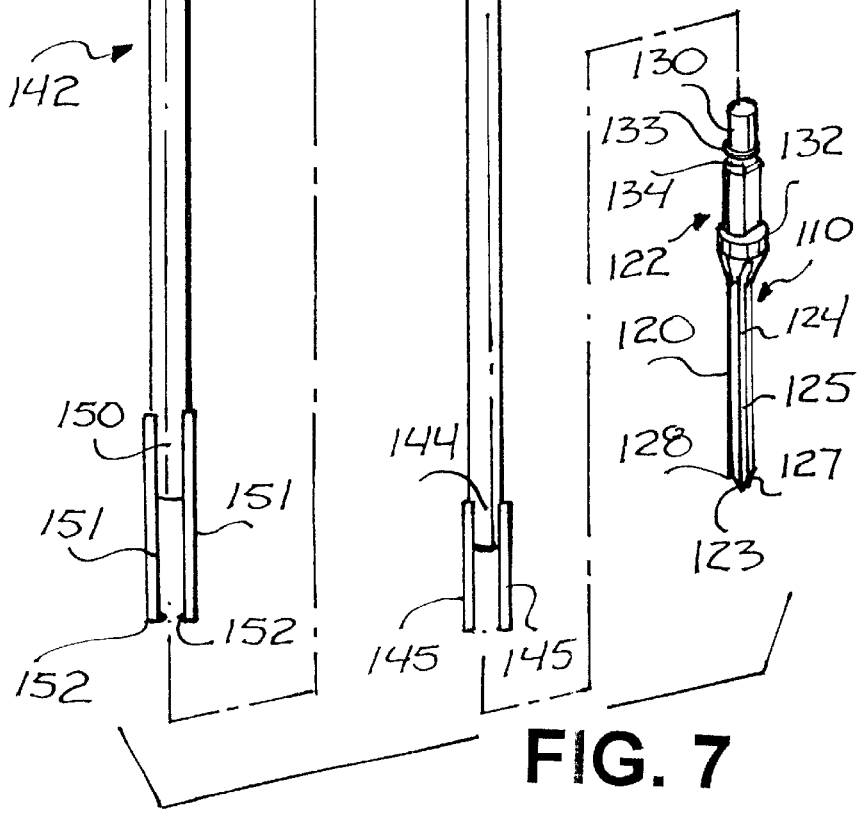
FIG. 7 is an exploded perspective view of another embodiment of a drill bit and inserter.

Referring to FIG. 7, a drill bit 110 and inserter 112 are illustrated. Drill bit 110 includes a cutting shank 120 having an attachment head 122 at one end and a tip 123 at an opposing end. Cutting shank 120 flares proximate attachment head 122, to substantially match the diameter thereof. At least one flute 124 extends the length of cutting shank 120 from tip 123 to attachment head 122. Flute 124 has a sharp edge 125 extending its entire length except at tip 123. Both edges of flute 124 can be sharp if desired. Rounded or dull edges 127 are formed at tip 123. The transition between sharp edge 125 and dull edges 127 is preferably located at point 128 where cutting shank 120 reaches a uniform width. Sharp edge 125 can start further back toward attachment head 122, as described in the previous embodiment. Drill bit 110 to this point is generally identical to drill bit 10 and operates in the same manner.

Still referring to FIG. 7, drill bit 110 is attached to inserter 112 by attachment head 122. Attachment head 122 includes an attachment shank 130 extending from a portion 132 terminating the flared end of cutting shank 120. Attachment shank 130 has a smaller diameter than portion 132, and is divided by an enlargement 133 forming a groove 134. Enlargement 133 also has a smaller diameter than portion 132.

Inserter 112 includes a receiver 140 and a securing sleeve 142. Receiver 140 has a shank end 143 for receipt within the chuck of a drill, and a receiver end 144 with a pair of tines 145 extending therefrom. Attachment shank 130 is fitted to be received between tines 145. In this embodiment, attachment shank 130 includes flattened sides which are captured between tines 145. Thus, relative rotation between drill bit 110 and receiver 140 is prevented.

Securing sleeve 142 is generally tubular and has an attachment end 150 from which extend a pair of tines 151 terminating in inwardly directed flanges 152 and an opposing end 153. Securing sleeve 142 has an inner diameter large enough to accommodate receiver 140 inserted through attachment end 150. Removal of receiver 140 through end 153 is prevented by tines 145 engaging attachment end 150. Tines 151 are positioned between tines 145 and engage groove 134 of drill bit 110. Shank end 143 passes through opposing end 153.

As with the previous embodiments, receiver 140 and sleeve 142 interact to form inserter 112, firmly attaching drill bit 110 to a drill but allowing a toggle or pivoting movement of drill bit 110 due to the multiple loose connections.

Various changes and modifications to the embodiments herein chosen for purposes of illustration will readily occur to those skilled in the art. To the extent that such modifications and variations do not depart from the spirit of the invention, they are intended to be included within the scope thereof which is assessed only by a fair interpretation of the following claims.

Having fully described the invention in such clear and concise terms as to enable those skilled in the art to understand and practice the same, the invention claimed is:

1. A vertebral drill bit for forming a pathway through a pedicle into a vertebral body, comprising:

a cutting shank having a first end and a second end;

an attachment head at the first end of the cutting shank;

a tip at the second end of the cutting shank;

a point at which the diameter of the cutting shank at the second end begins to get smaller to form the tip;

a flute formed in the cutting shank and extending from the first end to the tip;

an edge of the flute from the first end to proximate the point being sharp for cutting; and edges of the flute from the point to the tip being rounded.

2. A vertebral drill bit as claimed in claim 1 wherein the first end of the cutting shank is flared outwardly to a larger diameter with a corresponding outward flare in the flute and the edge of the flute from the first end to proximate the point.

3. A vertebral drill bit as claimed in claim 2 wherein the attachment head includes a socket formed therein.

4. A vertebral drill bit as claimed in claim 2 wherein the attachment head includes a portion terminating the first end and having a diameter substantially the same as the larger diameter of the flared first end.

5. A vertebral drill bit as claimed in claim 4 wherein the attachment head includes a socket formed therein.

6. A vertebral drill bit as claimed in claim 4 wherein the attachment head further includes an attachment shank extending from the portion, the attachment shank divided by a groove.

7. A vertebral drill bit as claimed in claim 4 wherein the attachment head further includes an attachment shank extending from the portion, the attachment shank divided by an enlargement forming a groove adjacent the portion.

8. A vertebral drill bit as claimed in claim 1 further including an inserter for coupling the drill bit to a drill.

9. A vertebral drill bit as claimed in claim 8 wherein the inserter includes a chuck end and a receiver end.

10. A vertebral drill bit as claimed in claim 8 wherein the inserter includes a receiver received within a securing sleeve.

11. A vertebral drill bit as claimed in claim 10 wherein the receiver includes an end coupled to the attachment head preventing relative rotation between the drill bit and the receiver and the securing sleeve including means for gripping the attachment head.

12. A vertebral drill bit for forming a pathway through a pedicle into a vertebral body, comprising:

a cutting shank having a first end and a second end;

an attachment head including a portion terminating the first end of the cutting shank and having an enlarged diameter;

a tip at the second end of the cutting shank;

a point at which the diameter of the cutting shank at the second end begins to get smaller to form the tip;

a flute formed in the cutting shank and extending from the first end to the tip;

an edge of the flute from the first end to proximate the point being sharp for cutting;

edges of the flute from the point to the tip being rounded; and an inserter engaging the attachment head for coupling the drill bit to a drill.

13. A vertebral drill bit as claimed in claim 12 wherein the attachment head includes a socket formed therein and the inserter includes a chuck end receivable by a chuck of a drill and a receiver end inserted into the socket.

14. A vertebral drill bit as claimed in claim 12 wherein the attachment head further includes an attachment shank extending from the portion, the attachment shank divided by an enlargement forming a groove adjacent the portion.

15. A vertebral drill bit as claimed in claim 14 wherein the inserter includes a receiver received within a securing sleeve.

16. A vertebral drill bit as claimed in claim 15 wherein the receiver includes an end coupled to the attachment head preventing relative rotation between the drill bit and the receiver and the securing sleeve including an inwardly directed flange at one end inserted into the groove for gripping the attachment head.

17. A vertebral drill bit as claimed in claim 12 wherein the first end of the cutting shank is flared outwardly to a larger diameter with a corresponding outward flare in the flute and the edge of the flute from the first end to proximate the point.

* * * * *